United States Patent [19]

Garbrecht et al.

[11] Patent Number: 4,968,802

[45] Date of Patent: Nov. 6, 1990

[54] PROCESS OF MAKING ALKOXY CYCLOALKANOL ESTERS OF DIHYDROLYSERGIC ACID

[75] Inventors: William L. Garbrecht; Gifford P. Marzoni, both of Indianapolis; Kathleen R. Whitten, Zionsville, all of Ind.

[73] Assignee: Eli Lilly and Company, Indianapolis, Ind.

[21] Appl. No.: 463,101

[22] Filed: Jan. 10, 1990

Related U.S. Application Data

[60] Division of Ser. No. 342,280, Apr. 24, 1989, Pat. No. 4,914,100, which is a division of Ser. No. 251,412, Sep. 29, 1988, Pat. No. 4,847,261, which is a continuation of Ser. No. 94,999, Sep. 10, 1987, abandoned, which is a division of Ser. No. 782,340, Oct. 1, 1985, Pat. No. 4,714,704.

[51] Int. Cl.$^5$ .......................................... C07D 457/04
[52] U.S. Cl. .......................................................... 546/69
[58] Field of Search .............................................. 546/69

[56] References Cited

U.S. PATENT DOCUMENTS

| | | | |
|---|---|---|---|
| 3,113,133 | 12/1963 | Hofmann et al. | 546/69 |
| 3,183,234 | 5/1965 | Garbrecht et al. | 546/69 |
| 3,228,941 | 1/1966 | Bernardi et al. | 546/69 |
| 3,580,916 | 5/1971 | Garbrecht | 546/69 |
| 3,704,233 | 11/1972 | Eich et al. | 546/67 |
| 4,230,859 | 10/1980 | Rucman | 546/69 |
| 4,563,461 | 1/1986 | Cohen et al. | 546/69 |
| 4,713,384 | 12/1987 | Cohen et al. | 546/69 |
| 4,713,385 | 12/1987 | Marzoni et al. | 546/69 |
| 4,734,501 | 3/1988 | Marzoni | 546/69 |
| 4,914,100 | 4/1990 | Garbrecht et al. | 546/69 |

FOREIGN PATENT DOCUMENTS

122044 10/1984 European Pat. Off.

OTHER PUBLICATIONS

Pfeffer et al., Tetrahedron Letters, No. 40, pp. 4063–4066, 1972.
Shaw et al., J. Org. Chem., vol. 43, No. 5, 1978, p. 1071.
Sowinski et al., J. Org. Chem. vol. 44, No. 14, 1979, p. 2369.
Misner, Chem Abst. 107-78140t (1987).
Cohen et al., J.P.E.T., 227, 327 (1983).
Cohen et al., J.P.E.T. 232, 770 (1984).
Lemberger et al., Life Sci., 35, 71 (1984).
Cohen et al., Drug Dev. Res., 5, 313 (1985).
Hingten et al., Abstract 37.4, Soc. for Neurosci. (13th Annual Meeting, Nov., 1983).

*Primary Examiner*—Cecilia Shen
*Attorney, Agent, or Firm*—William C. Martens; Leroy Whitaker

[57] ABSTRACT

Alkoxycycloalkyl esters of 1-substituted-6-$C_{1-4}$ straight chain alkyl (or allyl)ergoline-8$\beta$-carboxylic acids, useful as 5HT receptor antagonists.

1 Claim, No Drawings

PROCESS OF MAKING ALKOXY CYCLOALKANOL ESTERS OF DIHYDROLYSERGIC ACID

This application is a division of application Ser. No. 342,280 filed Apr. 24, 1989, now U.S. Pat. No. 4,914,100 which is a division of Ser. No. 251,412 filed Sep. 29, 1988, U.S. Pat. No. 4,847,261, which is a continuation of Ser. No. 094,999 filed Sep. 10, 1987, now abandoned, which is a dividios of Ser. No. 782,340 filed Oct. 1, 1985, now U.S. Pat. No. 4,714,704.

BACKGROUND OF THE INVENTION

Garbrecht, U.S. Pat. No. 3,580,916, discloses a group of lysergic (I) and 9,10-dihydrolysergic acid (II) esters formed with various open chain and cyclic diols. The following structures summarize the disclosure in Garbrecht.

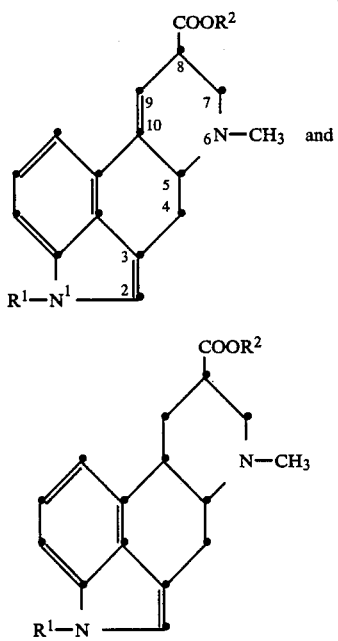

wherein $R^1$ is H, $C_{1-3}$ alkyl, allyl or benzyl and $R^2$ is $C_{2-C8}$ monohydroxyalkyl, $C_{2-8}$ dihydroxyalkyl or $C_{5-11}$ monohydroxycycloalkyl having from 5-8 ring carbons. The compounds are useful as serotonin antagonists, the patent stating that "In animals, the compounds act as neurosedatives. . . and are therefore useful in calming. . . animals". The use of compounds according to II, wherein $R^2$ is mono or dihydroxyalkyl, in migraine and other disease states characterized by an excess of peripheral 5HT is disclosed in EPO 122,044 published Oct. 17, 1984.

The interest in the Garbrecht compounds has thus been intensified by the finding that they had excellent peripheral serotonin antagonist activity against 5HT$_2$ receptors and lacked interaction, whether as agonists or antagonists, with other receptors, particularly alpha$_1$ receptors.

The most active peripheral serotonin antagonist from Garbrecht was named 1-isopropyl-6-methyl-8β-(1-methyl-2-hydroxy)propoxycarbonyl-5R-ergoline (II in which $R^1$ is isopropyl and $R^2$ is 1-methyl 2-hydroxypropyl) or 1-methyl-2-hydroxypropyl 1-isopropyl-9,10dihydrolysergate. In the above name, 5R refers to the beta orientation of the C-5 hydrogen. The C-10 hydrogen is alpha--10R, and the beta orientation at C-8 is R and is the same as in either lysergic or 9,10-dihydrolysergic acid. Both of these acids have a 6-methyl group. An alternate name for the compound is 1-isopropyl-9,10-dihydrolysergic acid 1-methyl-2-hydroxypropyl ester. Cohen et al. *J.P.E.T.*, 227, 327 (1983) (Cohen I) reported that the above compound, given the code number LY53857, was a potent antagonist of vascular contraction to serotonin, which effect is mediated by 5HT$_2$ receptors. The compound had minimal affinity for vascular alpha adrenergic, dopaminergic and histaminergic receptors ($K_{dissoc.} \approx 10^{-10}$ vs $-10^{-5}$). Other papers on the pharmacologic properties of LY53857 include Cohen et al., *J.P.E.T.*, 232, 770 (1985) (Cohen III), Harriet Lemberger et al., *Life Sciences*, 35, 71 (1984), Cohen, *Drug Development Res.*, 5, 313 (1985), (Cohen IV). Cohen and Fuller, EPO 122,044 published 10-17-84, covers the use of hydroxyalkyl esters of 1-alkyl 9,10-dihydrolysergic acid as peripheral 5HT$_2$ receptor antagonists.

Four additional examples of ergolines with a substituent on the indole nitrogen are: U.S. Pat. No. 3,113,133, Hofmann et al., which discloses and claims esters and amides carrying an indole N substituent such as a lower alkyl or alkenyl group or an aralkyl group. The compounds are said to be useful as serotonin antagonists, in treating inflammatory, arthritic and allergic diseases and in treating carcinoid syndrome.

U.S. Pat. No. 3,249,617, Hofmann et al., which covers (indole) N-alkyl or allyl lysergic acids, useful as intermediates.

U.S. Pat. No. 3,228,941, Bernardi et al., which discloses and claims a group of (indole) N-methylergolines—amides, hydroxamides and amidines. The compounds are alleged to have oxytoxic, adrenolytic, hypotensive, sedative and antienteraminic action.

U.S. Pat. No. 4,230,859 to Rucman which discloses dihydrolysergic acids carrying a $C_{1-5}$ alkyl group on the indole nitrogen, useful as intermediates.

Finally, ergolines actually used in the treatment of migraine include the amides: ergotamine, methysergide and ergonovine.

None of the above references indicate that alkoxycycloalkanol esters of an N-alkylated dihydrolysergic acid would have peripheral serotonin antagonist properties.

SUMMARY OF THE INVENTION

This invention provides ergolines of the formula:

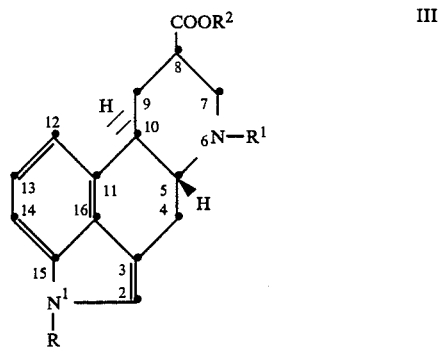

wherein R is primary or secondary $C_{1-8}$ alkyl, $C_{2-4}$ alkenyl-CH$_2$, $C_{3-8}$ cycloalkyl or $C_{3-6}$ cycloalkylsubstituted $C_{1-5}$ primary or secondary alkyl, the total number of carbon atoms in R not to exceed 8; $R^1$ is allyl, H or $C_{1-4}$ straight-chain alkyl; ie., methyl, ethyl, n-butyl, or n-propyl, and $R^2$ is $C_{1-3}$ alkoxy $C_{5-7}$ cycloalkyl; and pharmaceutically acceptable acid addition salts thereof. Compounds according to III, wherein $R^1$ is other than H, are central or peripheral serotonin 5HT$_2$ receptor antagonists lacking interaction at 5HT blocking doses with other receptors. Compounds wherein $R^1$ is H are primarily intermediates.

Groups which R represents include methyl, ethyl, allyl, n-propyl, isopropyl, crotyl, methallyl, n-hexyl, sec-amyl, sec-octyl, n-heptyl, 2,4-dimethylpentyl, 2-ethylpentyl, cyclopropyl, cyclopropylmethyl, cyclopentyl methyl, 2-cyclobutyl ethyl, cyclohexyl, isobutyl, sec.-butyl, 3-methyl-2-butyl, isoamyl, 2methylhexyl, 3-methylhexyl, 4-methylhexyl(isohexyl), 2-hexyl, 3-hexyl, n-heptyl, 2-heptyl, 3-heptyl, 4heptyl, n-octyl, 2-octyl, 3-octyl, 4-octyl, isooctyl, 2-methylheptyl, 3-methyl-2-heptyl, and the like. Illustrative of the groups which $R^2$ represents include 4-methoxycyclohexyl, 3-ethoxycyclohexyl, 3-methoxycyclopentyl, 3-methoxycycloheptyl, 3-n-propoxycycloheptyl, 3-ethoxycyclopentyl, 4-isopropoxycyclohexyl, 2-methoxycycloheptyl and the like.

Compounds according to the above formula are named as ergoline derivatives in which the trans(−) or 5R,10R configuration of the bridgehead hydrogens is specified (The same configuration as in the naturally-occurring 9,10-dihydro ergot alkaloids). In U.S. Pat. No. 3,580,916, a different naming system is used; the basic ring system is named as a 6aR,10aR-4,6,6a,7,8,9,10,10a-octahydroindolo4,3-f,g]quinoline. Illustratively, by the alternate naming system 9,10-dihydrolysergic acid becomes 6aR,10aR-7-methyl-4,6,6a,7,8,9,10,10a-octahydroindolo[4,3-f,g]quinoline9β-carboxylic dihydrolysergic acid is 6-methyl-8β-carboxyergoline. We prefer to use the trivial name "ergoline" with the numbering system specified in III above for compounds in which $R^1$ is other than methyl and the 9,10-dihydrolysergic acid nomenclature for 6-methyl derivatives.

In addition, in 9,10-dihydrolysergic acid, the C-8 carboxyl is beta or R. Thus, again using the ergoline naming system, derivatives of 9,10-dihydroproperties. lysergic acid become derivatives of 5R,8R,10R(or 5β,8β,10α) 6-methylergoline-8β-carboxylic acid.

While the configuration at asymmetric carbons 5,8 and 10 in formula III is set (5β,8βand 10β), generally speaking, the alkoxycycloalkanol ester group contains two additional asymmetric carbons. For example, 3-methoxycyclohexanol exists as two racemates, each racemate containing two enantiomers or stereoisomers. However, where the alkoxycycloalkanol possesses a plane of symmetry, as in a 4-alkoxycyclohexanol, mirror images turn out to be superimposable, and the compound actually exists in only two forms. These forms are designated as the cis form and the trans form, drawn for convenience in two dimensions as IVa and IVb.

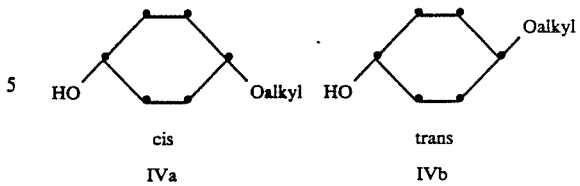

When a monoester of a 1-substituted-9,10-dihydrolysergic acid is formed with a cis or trans 4-alkoxycycloalkanol, the product will be a single geometrical isomer. In general, the two esters in this instance will also be named, for the sake of simplicity, as cis and trans 4-alkoxycyclohexyl esters.

This invention contemplates all such forms useful as peripheral serotonin antagonists; that is, the individual diastereoisomers and geometrical isomers as well as racemates.

Pharmaceutically-acceptable acid addition salts of the compounds of formula III include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenyl-butyrate, citrate, lactate, β-hydroxybutyrate, glycollate, malate, tartrate, methanesulfonate, propane-sulfonate, naphthalene-1-sulfonate, naphthalene-2sulfonate and the like salts.

Illustrative compounds of this invention include:
30 1-methyl-6-ethyl-8β-(2-methoxy)cyclopentyloxycarbonylergoline hydrochloride
1-n-propyl-6-allyl-8β-(3-ethoxy)cycloheptyloxycarbonylergoline sulfate
4-methoxycyclohexyl 1-methyl-9,10-dihydrolysergate phosphate
3-methoxycyclohexyl 1-n-octyl-9,10-dihydrolysergate maleate hexyloxycarbonylergoline hydrobromide
1-allyl-6-ethyl-8β-(4-ethoxy)cycloheptyloxycarbonylergoline succinate and the like.

Preferred embodiments of this invention are those in which R is isopropyl; in which $R^2$ is methoxycyclohexyl; or in which $R^2$ is 4-methoxycyclohexyl.

The preparation of compounds represented by formula III above is the general method of U.S. Pat. No. 3,580,916. According to this procedure, dihydrolysergic acid is first alkylated on the indole nitrogen using standard procedures—base plus an alkyl halide. Liquid ammonia is a convenient solvent with sodamide as the base and primary or secondary $C_{1-8}$ alkyl, $C_{3-8}$ cycloalkyl or $C_{3-6}$ substituted $C_{1-5}$ primary or secondary alkyl iodide or a $C_{2-4}$ alkenyl chloride or bromide as the alkylating agent. (See also U.S. Pat. No. 3,183,234-Garbrecht and Lin which contains general directions and a specific example of the above alkylation procedure).

An alternate alkylation procedure whereby an arylsulfonate is used in the presence of an alkali metal hydroxide is more fully described in the copending application of Marzoni Serial No. 782,339 filed this even date. According to this procedure, an arylsulfonate of the structure R—O—SO$_2$—phenyl—Y, wherein Y is H, 4-CH$_3$, 4-Br, 4-NO$_2$ and the like, is reacted with 9,10-dihydrolysergic acid in an aprotic solvent, conveniently DMSO, in the presence of sodium or potassium hydroxide.

With the indole nitrogen substituent in place, the next step in the synthetic procedure is esterification. This procedure requires relatively mild reaction conditions according to U.S. Pat. No. 3,580,916. The reaction is, however, an otherwise standard acid-catalyzed esterification. The free acid and alkoxycycloalkanol are the reactants and a convenient work-up of the esterification mixture involves partitioning between water and a water-immiscible solvent; (CH$_2$Cl)$_2$ for example.

A preferred procedure, however, is to use a novel synthetic step whereby the free 9,10-dihydrolysergic acid is reacted with a sulfonate of the alkoxycycloalkanol; ie, R$^2$—O—SO$_2$—Z, wherein Z is C$_{1-3}$ alkyl, phenyl or substituted phenyl wherein said substituents can be lower alkyl (CH$_3$, C$_2$H$_5$), nitro, halo(Br,Cl), alkoxy (CH$_3$O) and the like, in the presence of excess potassium carbonate or similar base in an aprotic solvent. The tosylate ester is preferred. The quantity of base must be sufficient to form a salt with the lysergic acid carboxyl plus sufficient to scavenge any sulfonic acid by-product. The reaction is applicable not only to the preparation of alkoxycycloalkyl esters but also to the preparation of the cycloalkyl and ketocycloalkyl esters of Whitten et al. Serial No. 782,337, filed this even date. In fact the reaction is generally applicable to the preparation of carbocyclic acid esters of C$_{5-7}$ cycloalkanols. Procedures hitherto available for the preparation of such esters have given low yields, and in some instances, esterification was not observed--see Shaw et al., J. Org. Chem., 43, 1017 (1978) 39, 1968 (1974), Sowinski et al, ibid, 44, 2369 (1979), Pfeffer et al Tetrahedron Letters, 4063 (1972) or Liotta et al, ibid, 2417 (1974).

If the desired final product is not a 9,10-dihydrolysergic acid ester (ie; not a 1-R-6-methylergoline-8β-carboxylic acid ester), but is a 6-ethyl, 6-n-propyl, 6-n-butyl, 6-allyl or the like derivative, the replacement of the 6-methyl group must take place prior to the final esterification with an alkoxycycloalkanol. In this procedure, we prefer to use a lower alkyl (methyl or ethyl) ester of a 1-R-9,10-dihydrolysergic acid. Replacement of the 6-methyl group with ethyl, n-propyl, allyl, n-amyl, n-butyl, n-hexyl, or the like, can be carried out by the procedure of Kornfeld and Bach, U.S. Pat. No. 4,166,182, whereby the N-methyl group is reacted with cyanogen bromide to form an N-cyano derivative. The cyano group can be removed by hydrogenation using zinc dust and hydrochloric acid. Alternatively basic hydrolysis can be used. Either procedure provides a secondary amine group at 6, but also a free 8β-carboxylic acid since the hydrolysis also saponifies the 8β-lower alkyl ester group. Next, reesterification with the desired R$^2$OH alkoxycycloalkanol is carried out followed by alkylation or allylation at N-6 using an allyl chloride or alkyl iodide in the presence of base, conveniently in DMF solution.

This procedure is graphically illustrated in Reaction Scheme 1 below.

Reaction Scheme 1

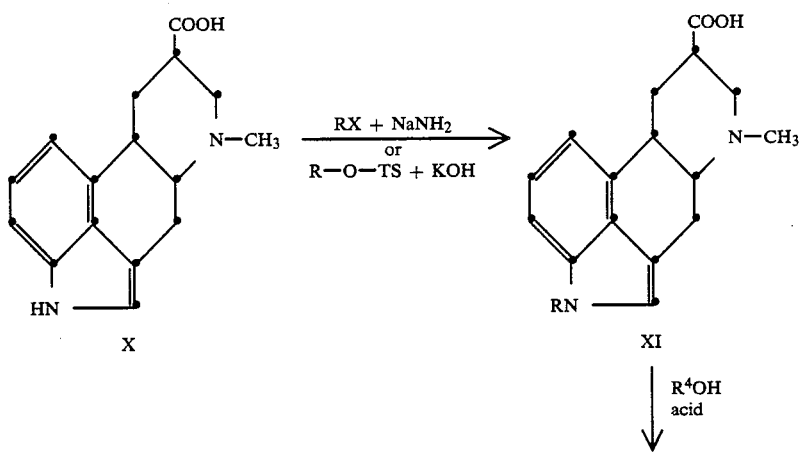

Reaction Scheme 1

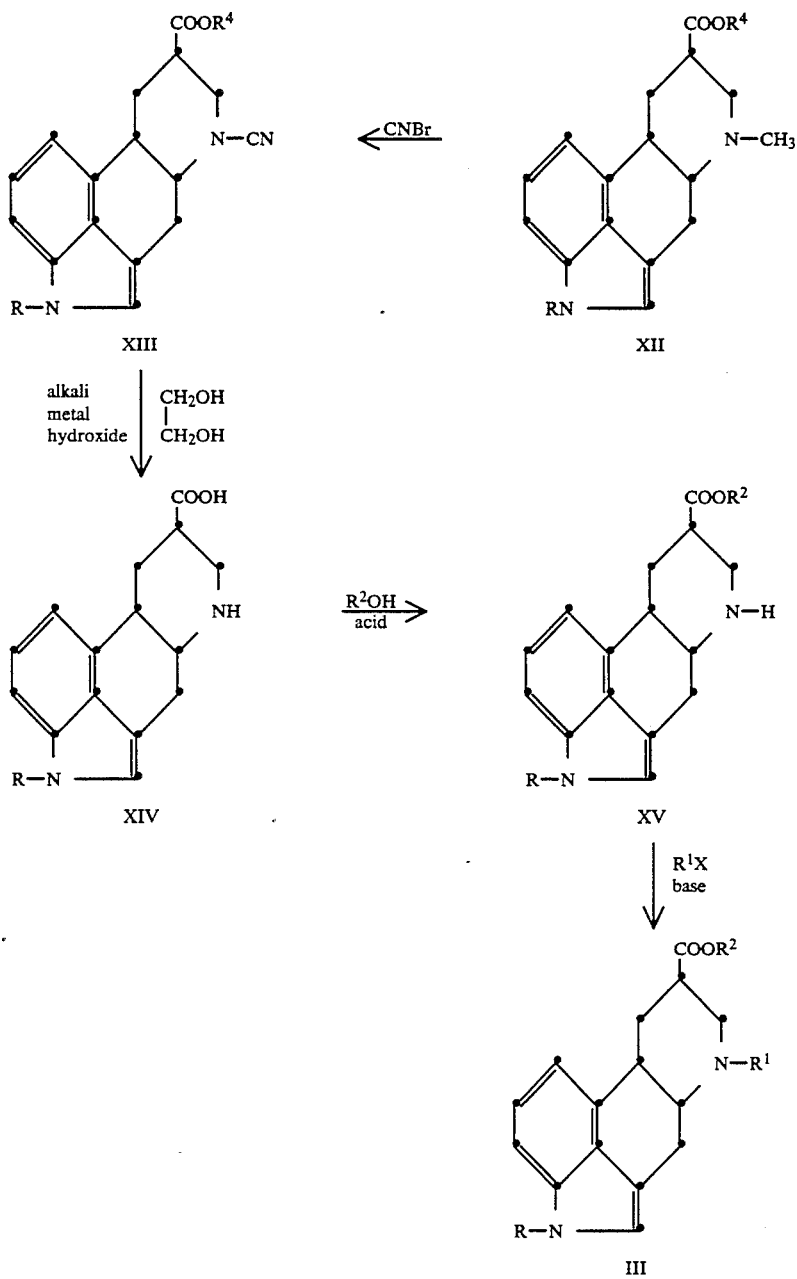

More specifically, in the above Reaction Scheme, 9,10-dihydrolysergic acid (X) is alkylated on the indole nitrogen with an alkyl ($C_{1-8}$ alkyl) halide, a $C_{2-4}$ alkenyl-$CH_2$ halide, a $C_{3-6}$ cycloalkyl halide or a $C_{3-6}$ cycloalkyl-$C_{1-5}$ alkyl halide, using sodamide to create the reactive anion or preferably using an aryl sulfonate such as a p-tosylate in the presence of potassium hydroxide in DMSO. The $N^1$ product (XI) is then esterified with a lower alkanol $R^4OH$ (a $C_{1-2}$ alkanol preferably) to yield the 1-R ester (XII). This intermediate is then reacted with CNBr by standard procedures to replace the methyl group and form an 6-cyano derivative (XIII). Removal of the cyano group under the preferred basic conditions yields a 1-substituted-9,10-dihydro-6-desmethyllysergic acid (XIV), since the basic conditions also saponifies the C-8 ester group. Next, the 1-R-6-desmethyldihydrolysergic acid is re-esterified with a desired alkoxy $C_{5-7}$ cycloalkanol or a tosyl ester thereof to yield the $N^6$-desmethyl ester (XV). The piperidine ring nitrogen ($N^6$) is then realkylated with a $C_{1-4}$ alkyl or allyl halide in the presence of base under standard conditions to yield the compounds of this invention (III).

It might seem redundant to realkylate at $N^6$ with a methyl group since that group is present in the 9,10-dihydrolysergic acid starting material. However, the process would enable one to insert a "tagged" ($C^{14}$ or $H^3$) methyl group for metabolic studies.

Although the above reaction sequence has been illustrated with reference to preparing alkoxycycloalkyl esters, it is apparent that the procedure is readily adaptable to the provision of 1,6-dialkyl ergoline carboxylic acid esters formed with open chain diols or ketoalkanols of the formula $R^6$—$CHR^5OH$ wherein $R^5$ is H, $C_{1-3}$ alkoxymethyl or $CH_3$ and $R^6$-is hydroxy $C_{1-3}$ alkyl, or keto $C_{1-3}$ alkyl. Such process is disclosed in the co-pending application of Whitten et al Serial No. 782,337, filed this even date.

The following examples illustrate the preparation of compounds according to III above.

EXAMPLE 1

Preparation of Trans-4-methoxycyclohexyl 1-Isopropyl-9,10-dihydrolysergate

A reaction mixture, prepared from 1 g of 1-isopropyl-9,10-dihydrolysergic acid, 1.77 g of potassium carbonate and 15 ml of DMF, was heated to about 70° C. 3.28 g of cis-4-methoxycyclohexyl tosylate were added. After about 18 hours, at 70° C., HPLC (reverse phase, 3:1 acetonitrile/0.1M aqueous ammonium acetate) indicated that the reaction was about 87% complete. The reaction mixture was then partitioned between 100 ml of distilled water and 100 ml of ethyl acetate. TLC (Chloroform/methanol/acetic acid, 18:6:1) indicated no desired product in the aqueous layer. The organic layer was extracted twice with 50 ml portions of distilled water and was then dried. Evaporation of the solvent gave 1.37 g of a 16:84 mixture of the cis and trans-4-methoxycyclohexyl 1-isopropyl-9,10-dihydrolysergate. The residue was dissolved in 15 ml of anhydrous ethanol containing 0.37 g of maleic acid. 250 ml of diethyl ether were added, whereupon a crystalline maleate began to form. The mixture was chilled overnight at about 0° C. and was then filtered. The filter cake was washed with ether and then dried. Assay indicated 91.4% trans and 8.6% cis esters; wt =0.86 g. This residue was dissolved in 35 ml of anhydrous ethanol and 400 ml of ether added. This time, the crystalline product was 8.4% cis and 93.6% trans; wt =.74 g. Recrystallization of this residue from ethyl acetate/toluene gave a residue which contained 5.6% cis and 94.4% trans esters. This residue was dissolved in 27 ml of anhydrous ethanol and 300 ml of ether added. Crystals thus produced weighed 0.48 g and contained 3.6% cis and 96.4% trans ester. The process was repeated using 21 ml of anhydrous ethanol and 250 ml of ether. 0.38 g of 4-methoxycyclohexyl 1-isopropyl-9,10-dihydro-lysergate maleate were obtained which contained 2% cis and 98% trans ester; mp =172° C. —173° C.; molecular ion (free base) at 424.

Analysis: Calc.: C., 66.65; H, 7.46; N, 5.18;
Found: C, 66.50; H, 7.56; N, 5.08.

EXAMPLE 2

Preparation of Cis-4-methoxycyclohexyl-1-Isopropyl-9,10-dihydrolysergate.

4-Methoxycyclohexanol (27.9 g) was reacted with 1-isopropyl-9,10-di-hydrolysergic acid (6.24 g) and p-toluenesulfonic acid (3.8 g) at room temperature for 3 days. It was then heated at about 90° C for 3 hours. At this time, HPLC analysis showed 19% unreacted lysergic acid, 70% 4-methoxycyclohexyl ester and 4% desmethyl compound (4-hydroxycyclohexyl ester). The reaction mixture was dissolved in $(CH_2Cl)_2$ and the organic solution washed with dilute ammonium hydroxide (pH ≅10). The crude product was isolated by evaporation of the organic solvent. It was treated with an excess of maleic acid and the maleate salt thus formed was crystallized from methanol/ether. The crystals were dissolved in boiling methanol, the hot solution treated with decolorizing charcoal and filtered. Addition of ether to the filtrate yielded 1.2 g of crystalline cis-4-methoxycyclohexyl 1-isopropyl-9,10-dihydrolysergate maleate (90% pure). A second crop, weight 2.26 g, was shown by HPLC to be 86% pure. The combined fractions were purified by preparative HPLC [C-18, 50:50 $CH_3CN/NH_{40}Ac$ (1)]. The maleate salt was reformed. Recrystallization from methanol/ether gave 1.27 g of 99% pure cis isomer; molecular ion at 424.

Analysis: Calc.: C, 66.65; H, 7.46; N, 5.18;
Found: C, 66.38; H, 7.74; N, 5.37.

The preparation of starting materials is illustrated below.

PREPARATION I

Cis-4-methoxycyclohexyl Tosylate

A solution was prepared by dissolving 65.45 g of 4-methoxycyclohexanol in 81 ml of pyridine. The solution was cooled to about 10° C. 105.4 g of p-toluene sulfonyl chloride were added in batchwise fashion over 15 minute period. The reaction mixture was stirred for 1 hour in the range 10° C. —20° C. and 4 hours at 25° C.-30° C. at which time it was added to 500 ml of an ice/water mixture containing 100 ml of 12N hydrochloric acid. A precipitate which resulted was separated by filtration, and the filter cake washed with water. The wet filter cake was slurried with 300 ml of anhydrous ethanol. The slurry was warmed on the steam bath and then cooled at about 0° C. The chilled slurry was filtered and the filter cake washed with cold anhydrous ethanol; yield =106.9 g; 82.4% cis ester by HPLC (C-18; 60:40 methanol/$H_{20}$) Recrystallizations from pet. ether gave 81.62 g of 93.6% cis ester. A second recrystallization from anhydrous ethanol yielded 72.04 g of 98% cis 4-methoxycyclohexyltosylate melting at 85-7° C.

Analysis Calc.: C, 59.13; H, 7.09; N, 11.28;
Found: C, 59.32; H, 7.20; N, 11.49.

PREPARATION II

Preparation of Cis-4-methoxycyclohexanol

Following the procedure of *J. Org. Chem.*, 28 1923 (1963), 13.35 g of $AlCl_3$ and 125 ml of ether were stirred under $N_2$ 25 ml of 1M $LiAlH_4$ in ether were added by syringe to the solution. Next, 13 g of 4-methoxycyclohexanol in 50 ml of ether were added to the stirred mixture over a 30 minute period. The mixture was then allowed to settle. The supernate was removed. The solid remaining was washed three times with 25, 50 and 50 ml portions of ether. The solid precipitate was filtered and the filter cake thoroughly washed with ether. (The filtrate, and washings contained trans-4-methoxycyclohexanol). The dried precipitate (19.17 g) was slurried in 100 ml of ether. 100 ml of 10% sulfuric acid were slowly added thereto (30 minutes). The cis isomer obtained from the decompositions of the $AlCl_2$ complex was in the ether layer which was separated. The separated layer was washed successively with 100 ml water, 50 ml saturated aqueous sodium bicarbonate and 50 ml of brine. The ethereal solution was dried and the ether evaporated to yield 1.7 g of cis-4-methoxycyclo-hexanol. An additional 4 g were obtained from the water layer.

This invention also provides novel methods whereby 5HT$_2$ receptors are blocked. Such methods are potentially useful in treating disease states in which an excess of circulating serotonin is a major contributing cause. These disease states include hypertension, anorexia nervosa, depression, mania, carcinoid syndrome, migraine and vasospasm. The compounds according to III above show relatively slight affinity for other receptors, $\alpha_1$, $\alpha_2$, $\beta$, histamine, carbachol etc. and thus are highly selective in their action. Formulations in which a compound of this invention is an active ingredient also form another aspect of this invention.

In order to demonstrate that compounds according to formula III have an extremely high affinity for $5HT_2$ receptors, apparent dissociation constants ($K_B$) as a measure of affinity for $5HT_2$ receptors, expressed as the negative logarithm, have been determined according to the following protocol.

Male Wistar rats (150–300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer had the following makeup: (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen-5% $CO_2$ An initial optimum resting force of 1 and 4 g was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of antagonist for one hour. Responses to serotonin or to norepinephrine were then repeated in the presence of the antagonist. Contraction to serotonin was evaluated in the jugular vein since this tissue produces marked responses to serotonin in the absence of alpha receptors—see Cohen and Wiley, *J. Pharm. Exp. Ther.*, 205, 400 (1978). Alpha receptor antagonist activity was evaluated in the aorta.

Apparent antagonist dissociation constants were determined for each concentration of antagonist according to the following equation:

$$K_B = \frac{[B]}{[\text{dose ratio-1}]}$$

wherein [B] is the concentration of the antagonist and the dose ratio is the $ED_{50}$ of the agonist in the presence of the antagonist divided by the control $ED_{50}$ These results are then expressed as the negative logarithm of $K_B$. The $-\log K_B$ values obtained for compounds of this invention are given below in Table 1.

TABLE 1

Apparent Dissociation Constants for $5HT_2$ receptors determined in the rat jugular vein.

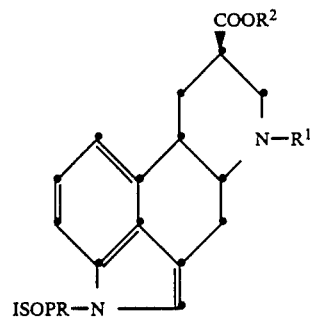

| Compound | | | $5HT_2$ |
|---|---|---|---|
| $R^1$ | $R^2$ | salt | $-\log K_b \pm$ S.E. |
| $CH_3$ | cis-4-methoxy-cyclohexyl | maleate | 9.54 ± 0.11(13) |
| $CH_3$ | trans-4-methoxy cyclohexyl | maleate | 8.96 ± 0.07(18) |

In mammals, hypertension may be mediated through $5HT_2$ receptors, Thus, compounds of formula III would be expected to lower blood pressure in humans as does ketanserin, another $5HT_2$ blocker, but without the side effects atrtibutable to alpha adrenergic receptor blockade of ketanserin.

In carrying out our novel therapeutic process, a pharmaceutically-accceptable salt of a drug according to formula III above formed with a non-toxic acid is administered orally or parenterally to a mammal with an excess of circulatory serotonin in which mammal is desirable to block $5HT_2$ receptors in order to alleviate symptoms attributable to excessive serotonin levels such as high blood pressure and migraine. For parenteral administration, a water soluble salt of the drug is dissolved in an isotonic salt solution and administered by the i.v. route. For oral administration, a pharmaceutically-acceptable salt of the drug is mixed with standard pharmaceutical excipients such as starch and loaded into capsules or made into tablets, each containing 0.1 to 100 mg of active drug. Dosage levels of from 0.1–10 mg/kg have been found to be effective in blocking $5HT_2$ receptors. Thus, the oral dosage would be administered 2–4 times per day, giving a daily dosage range of about 0.003 to about 10.0 mg./kg. per day.

Other oral dosage forms, suspensions, elixirs and tablets, can also be utilized and are preparable by standard procedures.

We claim:

1. A process for preparing a compound of the formula:

13

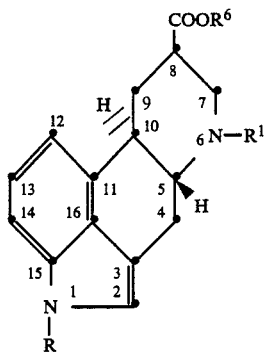

wherein R is primary or secondary $C_{1-8}$ alkyl, $CH_2$—$C_{2-4}$ alkenyl, $C_{3-8}$ cycloalkyl or $C_{3-6}$ cycloalkyl-substituted $C_{1-5}$ primary or secondary alkyl, the total number of carbon atoms in R not to exceed 8; $R^1$ is H or $C_{1-4}$ straight chain akyl, and $R^6$ is $C_{1-3}$ alkyloxy-$C_{5-7}$ cycloalkyl; $C_{5-7}$ cycloalkyl

14 or keto $C_{5-7}$ cylcloalkyl, which comprises reacting a compound of the formula

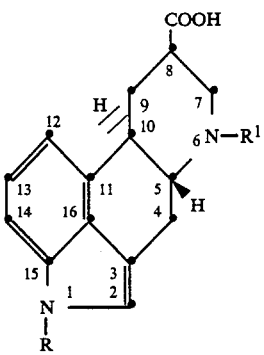

with a sulfonate ester ($R^6$—O—$SO_2$—Z) wherein Z is $C_{1-3}$ alkyl, phenyl or substituted phenyl wherein said substitutents are selected from the class consisting of lower alkyl, lower alkoxy, halo and nitro in the presence of a stoichiometric excess of base in an aprotic medium.

* * * * *